United States Patent
Chen et al.

(10) Patent No.: US 8,067,506 B2
(45) Date of Patent: Nov. 29, 2011

(54) WATER-SOLUBLE FLUORESCENT PARTICLE COMPRISING ENTANGLED FLUORESCENT POLYMER AND AMPHIPHILIC MOLECULE

(75) Inventors: Zhikuan Chen, Singapore (SG); Xu Li, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 690 days.

(21) Appl. No.: 12/065,478

(22) PCT Filed: Aug. 30, 2006

(86) PCT No.: PCT/SG2006/000251
§ 371 (c)(1),
(2), (4) Date: Feb. 29, 2008

(87) PCT Pub. No.: WO2007/027159
PCT Pub. Date: Mar. 8, 2007

(65) Prior Publication Data
US 2008/0242806 A1   Oct. 2, 2008

Related U.S. Application Data

(60) Provisional application No. 60/712,103, filed on Aug. 30, 2005.

(51) Int. Cl.
*C08G 63/00* (2006.01)
(52) U.S. Cl. ............ 525/450; 526/72; 526/256; 528/396
(58) Field of Classification Search .................. 525/450; 526/72, 256; 528/396
See application file for complete search history.

(56) References Cited

U.S. PATENT DOCUMENTS

| | | | |
|---|---|---|---|
| 2002/0193672 A1* | 12/2002 | Walsh et al. | 600/316 |
| 2004/0106163 A1* | 6/2004 | Workman et al. | 435/14 |
| 2005/0019265 A1* | 1/2005 | Hammer et al. | 424/9.61 |

FOREIGN PATENT DOCUMENTS

| | | |
|---|---|---|
| EP | 0 317 803 B1 | 5/1993 |
| WO | WO-02/076428 A1 | 10/2002 |
| WO | WO-2007/027159 A1 * | 3/2007 |

OTHER PUBLICATIONS

Pellegrino et al., "Hydrophobic Nanocrystals Coated with an Amphiphilic Polymer Shell: A General Route to Water Soluble Nanocrystals", Nano Letters, 2004, pp. 703-707, vol. 4, No. 4.*

(Continued)

*Primary Examiner* — Peter D. Mulcahy
*Assistant Examiner* — Henry Hu
(74) *Attorney, Agent, or Firm* — Klarquist Sparkman, LLP

(57) ABSTRACT

Water-soluble fluorescent particles are formed in a simple process. A mixture comprising a solvent, water, a fluorescent polymer dissolved in the solvent, and an amphiphilic molecule is provided. The fluorescent polymer comprises a hydrophobic segment. The amphiphilic molecule comprises hydrophilic and hydrophobic segments. The solvent is removed from the mixture to allow the fluorescent polymer and the amphiphilic molecule to entangle in the presence of water, thus forming the water-soluble fluorescent particles. In the formed particles, the hydrophilic segments of the amphiphilic molecule are entangled with one another, and the hydrophobic segments of the fluorescent polymer and amphiphilic molecule are entangled with one another. The amphiphilic molecule encapsulates the fluorescent polymer and at least some of the hydrophilic segments are exposed to render the particle soluble in water.

29 Claims, 11 Drawing Sheets

OTHER PUBLICATIONS

Teng et al., "Release Kinetics Studies of Aromatic Molecules into Water from Block Polymer Micelles", Macromolecules, 1998, pp. 3578-3587, vol. 31, No. 11.*

Pellegrino et al., "Hydrophobic Nanocrystals Coated with an Amphiphilic Polymer Shell: A General Route to Water Soluble Nanocrystals", Nano Letters, 2004, pp. 703-707, vol. 4, No. 4.*

Teng et al., "Release Kinetics Studies of Aromatic Molecules into Water from Block Polymer Micelles", Macromolecules, 1998, pp. 3578-3587, vol. 31, No. 11.

Zhang et al., "The effect of chain interpenetration on an ordering process in the early stage of polymer crystal nucleation", Polymer, 2006, pp. 5213-5219, vol. 47, No. 14.

Hao et al., "Synthesis and Comparison of Hyperbranched Aromatic Polyimides Having the Same Repeating Unit by AB2 Self-Polymerization and A2 + B3 Polymerization", Macromolecules, 2003, pp. 3519-3528, vol. 36, No. 10.

Shroff et al., "Assessment of NMR and Rheology for the Characterization of LCB in Essentially Linear Polyethylenes", Macromolecules, 2001, pp. 7362-7367, vol. 34, No. 21.

Charlesby, "Analysis of Macromolecular Structures by Pulsed NMR", Radiat. Phys. Chem., 1992, pp. 45-51, vol. 39, No. 1.

Pellegrino et al., "Hydrophobic Nanocrystals Coated with an Amphiphilic Polymer Shell: A General Route to Water Soluble Nanocrystals", Nano Letters, 2004, pp. 703-707, vol. 4, No. 4.

White et al., "Fluorescence techniques for drug delivery research: theory and practice", Advanced Drug Delivery Reviews, 2005, pp. 17-42, vol. 57.

Stephens et al., "Light Microscopy Techniques for Live Cell Imaging", Science, 2003, pp. 82-86, vol. 300.

Shah et al., "Molecular imaging of gene therapy for cancer", Gene Therapy, 2004, pp. 1175-1187, vol. 11.

Kojima et al., "Bioimaging of Nitric Oxide with Fluorescent Indicators Based on the Rhodamine Chromophore", Anal. Chem., 2001, pp. 1967-1973, vol. 73, No. 9.

Kojima et al., "Fluorescent Indicators for Imaging Nitric Oxide Production", Angew. Chem. Int. Ed., 1999, pp. 3209-3212, vol. 38, No. 21.

Lippincott-Schwartz et al., "Development and Use of Fluorescent Protein Markers in Living Cells", Science, 2003, pp. 87-91, vol. 300.

Heim et al., "Engineering green fluorescent protein for improved brightness, longer wavelengths and fluorescence resonance energy transfer", Current Biology, 1996, pp. 178-182, vol. 6.

Daly et al., "Fluorescent ligands, antibodies, and proteins for the study of receptors", Pharmacology & Therapeutics, 2003, pp. 101-108, vol. 100.

Gaylord et al., "DNA Hybridization Detection with Water-Soluble Conjugated Polymers and Chromophore-Labeled Single-Stranded DNA", J. Am. Chem. Soc., 2003, pp. 896-900, vol. 125.

Bruchez, Jr. et al., "Semiconductor Nanocrystals as Fluorescent Biological Labels", Science, 1998, pp. 2013-2016, vol. 281.

Chan et al., "Quantum Dot Bioconjugates for Ultrasensitive Nonisotopic Detection", Science, 1998, pp. 2016-2018, vol. 281.

Han et al., "Quantum-dot-tagged microbeads for multiplexed optical coding of biomolecules", Nature Biotechnology, 2001, pp. 631-635, vol. 19.

Zhong et al., "Composition-Tunable $Zn_xCd_{1-x}Se$ Nanocrystals with High Luminescence and Stability", J. Am. Chem. Soc., 2003, pp. 8589-8594, vol. 125.

Zhong et al., "Alloyed $Zn_xCd_{1-x}S$ Nanocrystals with Highly Narrow Luminescence Spectral Width", J. Am. Chem. Soc., 2003, pp. 13559-13563, vol. 125.

Kushon et al., "Detection of DNA Hybridization via Fluorescent Polymer Superquenching", Langmuir, 2002, pp. 7245-7249, vol. 18, No. 20.

* cited by examiner

POSS-PEO

WATER-SOLUBLE FLUORESCENT PARTICLE COMPRISING ENTANGLED FLUORESCENT POLYMER AND AMPHIPHILIC MOLECULE

CROSS REFERENCE TO RELATED APPLICATIONS

This applications claims the benefit of related U.S. Provisional Application Ser. No. 60/712,103, filed Aug. 30, 2005, the contents of which are incorporated herein by reference.

FIELD OF THE INVENTION

The present invention relates to fluorescent particles.

BACKGROUND OF THE INVENTION

Fluorescent particles are useful in various applications. For instance, fluorophores are useful as fluorescent probes, such as labels or tags, e.g., in many biochemical fields, such as drug and gene research, cell/microorganism imaging, disease diagnosis, analyte detection, and the like. Conventional fluorophores include organic dyes, green fluorescent proteins (GFP) and their mutants, water-soluble conjugated fluorescent polymers, quantum dots (QD), and the like.

However, conventional fluorophores have some drawbacks. For example, the manufacturing processes of multicolor organic dyes and GFPs are complicated. Further, the performance of these fluorophores often depends on the surrounding environment, thus rendering them unstable and unreliable, even unsuitable in certain environments. In addition, GFPs have low luminescence, especially in the blue and red spectral regions. Water-soluble conjugated fluorescent polymers, like organic dyes and GFPS, are sensitive to conditions of the external environment, such as pH values or ionic strength of the surrounding solution. Another problem is that many fluorophores, including many fluorescent polymers, cannot be dissolved in water to form a stable and homogenous solution, which significantly limits their application, as aqueous environments are the most common environments in nature.

A known technique of solubilizing hydrophobic fluorescent nanocrystals in aqueous solutions is to wrap nanocrystals with cross-linked amphiphilic polymers to form water-soluble QDs. However, this approach has the disadvantage of requiring complicated preparation steps, as the amphiphilic polymers not only have to form shells around the nanocrystal cores, the amphiphilic polymers also have to be cross-linked after they form the shells. Further, QDs have other shortcomings. The formation process of QDs typically requires elevated temperatures and it is difficult to produce QDs with both high luminescence and narrow emission spectra. In addition, QDs have limited application in certain fields, such as single-molecule imaging in live cells, which typically involves photobleaching or fluorescence blinking. As QDs have high photo-stability, they are difficult to photobleach. As QDs have long blinking intervals, they are unsuitable for use in fluorescence blinking procedures.

SUMMARY OF THE INVENTION

In accordance with a first aspect of the invention, there is provided a water-soluble fluorescent particle. The particle comprises a fluorescent polymer comprising a hydrophobic segment; and an amphiphilic molecule comprising hydrophilic segments and hydrophobic segments, the hydrophilic segments of the amphiphilic molecule being entangled with one another, the hydrophobic segments of the fluorescent polymer and the amphiphilic molecule being entangled with one another, wherein the amphiphilic molecule encapsulates the fluorescent polymer and at least some of the hydrophilic segments are exposed to render the particle soluble in water. The fluorescent particle may be used as a probe, such as for detecting, imaging, or tracking a target and may include a ligand for attaching the particle to a target.

According to another aspect of the invention, there is provided a process for preparing the water-soluble fluorescent particles described above. The process includes providing a mixture comprising a solvent, water, the fluorescent polymer dissolved in the solvent, and the amphiphilic molecule; and removing the solvent from the mixture to allow the fluorescent polymer and the amphiphilic molecule to entangle in the presence of water, thus forming the water-soluble fluorescent particle. The mixture may be prepared by mixing a solution with an aqueous liquid comprising water. The solution comprises the solvent and precursors for the fluorescent polymer and the amphiphilic molecule.

In accordance with further aspect of the present invention, there is provided a fluorescent probe comprising the above described particle.

In accordance with another aspect of the present invention, there is provided a solution which includes the above described particles dissolved in water.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

FIGS. 5A to 5C are transmission electron microscopic (TEM) images of exemplary fluorescent particles in aqueous solutions;

DETAILED DESCRIPTION

Figure 1:
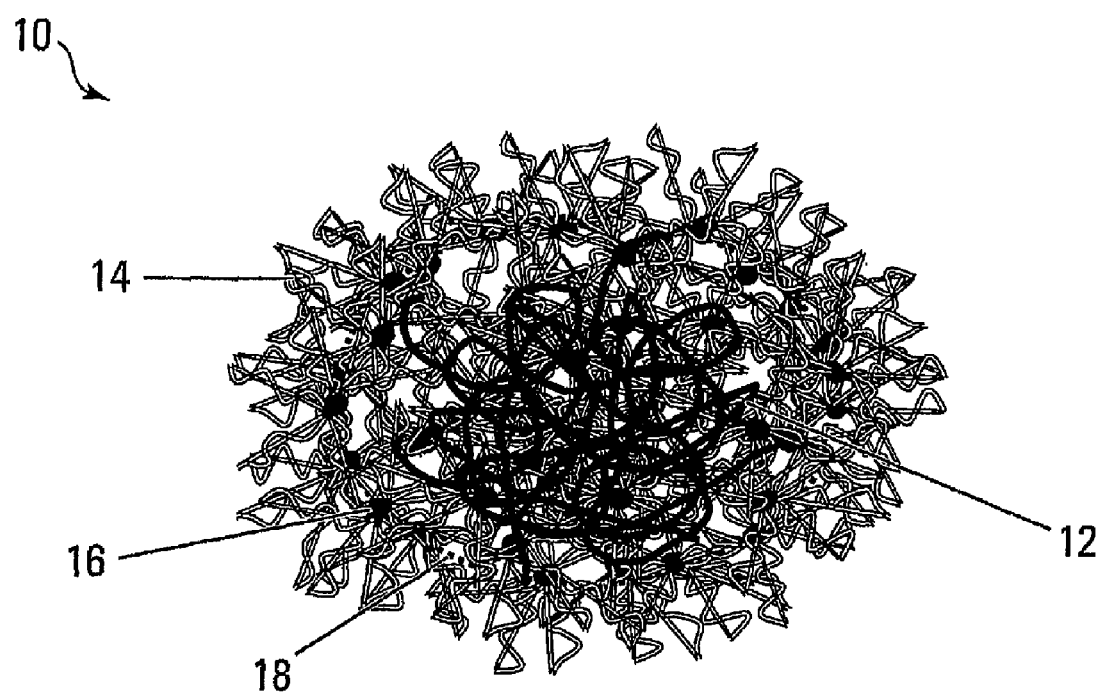
FIG. 1 is a schematic diagram of a fluorescent particle, exemplary of an embodiment of the present invention.

In overview, water-soluble fluorescent particles, such as the particle 10 schematically shown in FIG. 1, can be formed in a relatively simple procedure as described below. As illustrated, particle 10 may have a fluorescent polymer 12 (thick lines) and one or more amphiphilic molecules 14 (thin lines) that encapsulate fluorescent polymer 12. Fluorescent polymer 12 has one or more hydrophobic segments. Amphiphilic molecule 14 has both hydrophobic segments, such as hydrophobic blocks 16 (large black blocks), and hydrophilic segments, such as a hydrophilic backbone. The hydrophobic segments of fluorescent polymer 12 and the hydrophobic segments of amphiphilic molecule 14 are entangled with one another. The hydrophilic segments of amphiphilic molecules 14 are also entangled with one another. At least some of the hydrophilic segments of amphiphilic molecules 14 are exposed to render the particle 10 soluble in water. The dotted line 18 indicates a boundary which separates particle 10 into a mainly hydrophobic core region and a mainly hydrophilic shell region. The entanglement of the molecules is believed to make the physical structure of particle 10 stable, even when particle 10 is dissolved in an aqueous solution.

Fluorescent polymer 12 may include any suitable polymer molecules that are fluorescent and have one or more hydrophobic segments such that the fluorescent polymer molecules will not be sufficiently soluble in water to form a stable and homogenous solution. The fluorescent particle may include an encapsulated fluorescent polymer that has only hydrophobic segments, or both hydrophobic and hydrophilic segments. A hydrophilic segment of the fluorescent polymer, if present, may entangle with the hydrophilic segments of the amphiphilic molecules. In any case, the amount of the hydrophobic segment in the fluorescent polymer should be sufficient to ensure that on formation of the particle the fluorophore of the polymer is present in the mainly hydrophobic core region and thus encapsulated by the mainly hydrophilic shell region, and the fluorescent particles can be dissolved in water to form a stable, homogenous solution.

Different polymers may be chosen depending on the desired fluorescence properties of the resulting particles. For example, if it is desirable that the particle emits orange light, those skilled in the art will appreciate that suitable polymers may include polymers that can emit fluorescent light of a generally orange color on excitation, such as poly(2-methoxy-5-2'-ethyl-hexyloxy-1,4-phenylene vinylene) (MEH-PPV). In some applications, it may be desirable that the fluorescent polymers exhibit intense fluorescence. Particle 10 may include any number of molecules of the same fluorescent polymer. In different embodiments, a single particle may contain two or more different fluorescent polymers that exhibit distinct fluorescence responses such as distinct fluorescence emission spectra or distinct fluorescence absorption spectra, or both.

Fluorescent polymer 12 may have one or more component groups. Each component group may be one of arylene, heteroarylene, arylene vinylene, heteroarylene vinylene, arylene ethylene, heteroarylene ethylene, and the like, each of which may be a substituted or unsubstituted group. The arylene group may have one or more of O, S, N, Si, and P atoms. The arylene group may be connected to each other through a single bond or through a connecting group. The connecting group may be one of O, S, Si, N, P, and substituted or non-substituted alkylene. For example, a component group may be one of phenylene, thienylene, fluorenylene, spirobifluorenylene, indenofluorenylene, pyridylene, bipyridylene, carbazoylene, indenocarbazolylene, benzothiazolylene, oxadiazolylene, and the like. A component group may also be one of alkyl, alkoxy, alkenyl, alkynyl, alkylthio, alkylamino, dialkylamino, arylamino, diarylamino, amino group comprising a heteroaryl group, aryl ether, heteroaryl ether, aryl thioether, heteroaryl thioether, hydrogen, halogen, cyano, nitro, carbony, thionyl, sulphonyl, and perfluoroalkyl including its substituents.

For example, polyfluorenes (PF), polythiophenes (PTh), polyphenylenevinylenes (PPV), polyphenylene-ether (PPE), polyarylenevinylenes, polyaryleneethynylene, and their derivatives or copolymers may be suitable fluorescent polymers in different embodiments.

Figure 2:
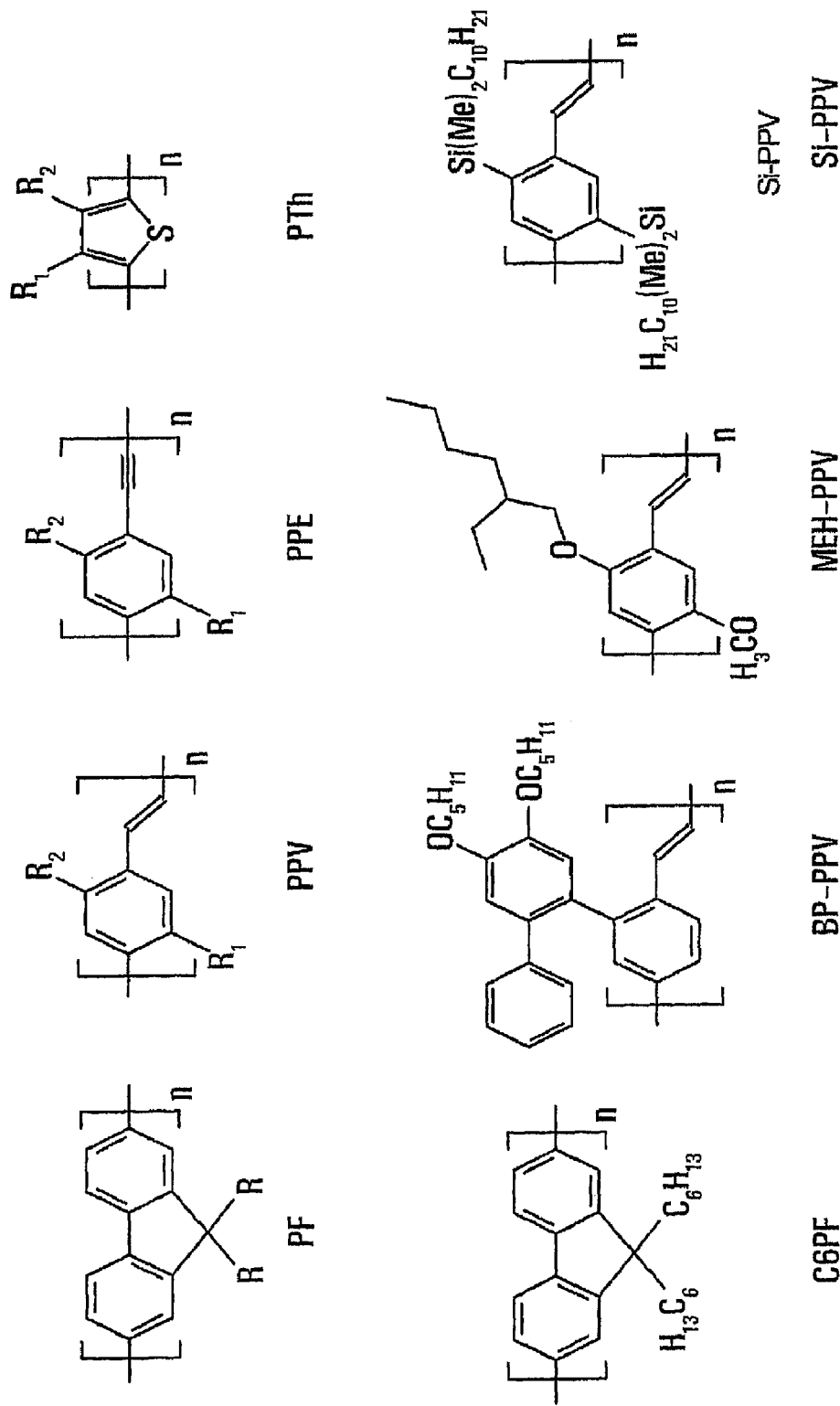
FIG. 2 shows chemical structures of exemplary fluorescent polymers.

FIG. 2 shows the chemical structures of some exemplary fluorescent polymers, which include PF, PPE, PTh, PPV, and their derivatives such as poly(9,9-dihexylfluorenyl-2,7-diyl) (C6PF), poly(2-(2'-phenyl-4',5'-di(3"-methyl-butyl)-phenyl-1,4-phenylenevinylene)) (BP-PPV), MEH-PPV, and poly(2,5-bisdimethyidecylsilyl)-1,4-phenylene vinylene (Si-PPV). In FIG. 2, "n" may have a value from 3 to 3000, such as from 3 to 1000. Each of R, $R_1$, and $R_2$ may be independently selected from hydrogen, halogen, and cyano. Each of R, $R_1$, and $R_2$ may also be independently selected from alkyl, alkoxy, alkylthio, alkylamino, alkenyl, alkynyl, aryl, heteroaryl, arylamino, heteroarylamino, aryloxy, heteroaryloxy, arylthio, heteroarylthio, aralkyl, heteroaralkyl, alkylsilyl, and alkylgermyl groups, each group being either substituted or unsubstituted. Each of the alkyl, alkoxy, alkylthio, alkylamino, and heteroalkyl groups may have 1 to 30 carbon atoms, such as 1 to 18 carbon atoms. Each of the alkenyl and alkynyl groups may have a chain length of 2 to 30 carbon atoms, such as 2 to 18 carbon atoms. Each of the aryl, arylthio, and aryloxy groups may have 6 to 60, such as 6 to 30, carbon atoms. The arylamino group may have 6 to 180 carbon atoms, such as 6 to 120 carbon atoms. Each of the heteroaryl, heteroaryloxy, and heteroarylthio group may have 3 to 120, such as 3 to 60 carbon atoms. The heteroarylamino group may have 3 to 180 carbon atoms, such as 3 to 120 carbon atoms.

Depending on the application, red, orange, yellow, green, or blue, fluorescent polymers may be selected. For instance, MEH-PPV, C6PF, BP-PPV, or the like, or any combination thereof, may be used as the fluorophore in particle 10.

Amphiphilic molecules 14 may be any suitable amphiphilic molecules that have hydrophilic and hydrophobic components. Amphiphilic molecules 14 may be biocompatible. For example, suitable amphiphilic molecules may include lipids and polymers such as copolymers, hyperbranched polymers, or dendritic polymers. Amphiphilic molecules 14 may have one or more hydrophilic segments and one or more hydrophobic segments. The hydrophilic and hydrophobic segments may form a block copolymer. The copolymer may have a backbone formed from hydrophobic segments, with hydrophilic segments attached to the hydrophobic backbone at various points. The copolymer may have a backbone formed from hydrophilic segments, with hydrophobic segments attached to the hydrophilic backbone. The backbone may also be formed from both hydrophobic and hydrophilic segments, with one or both of hydrophilic and hydrophobic graft segments attached thereto. As can be appreciated, graft polymers containing a hydrophilic backbone and hydrophobic side chains may also be suitable because in an aqueous solution such a polymer molecule can change its configuration so that the hydrophobic side chains of the graft polymer shrink or entangle into a core and hydrophilic segments of the polymer stretch out into the water phase to cover the core, exposing the hypdophilic segments to water and rendering the polymer soluble.

Figure 3A:
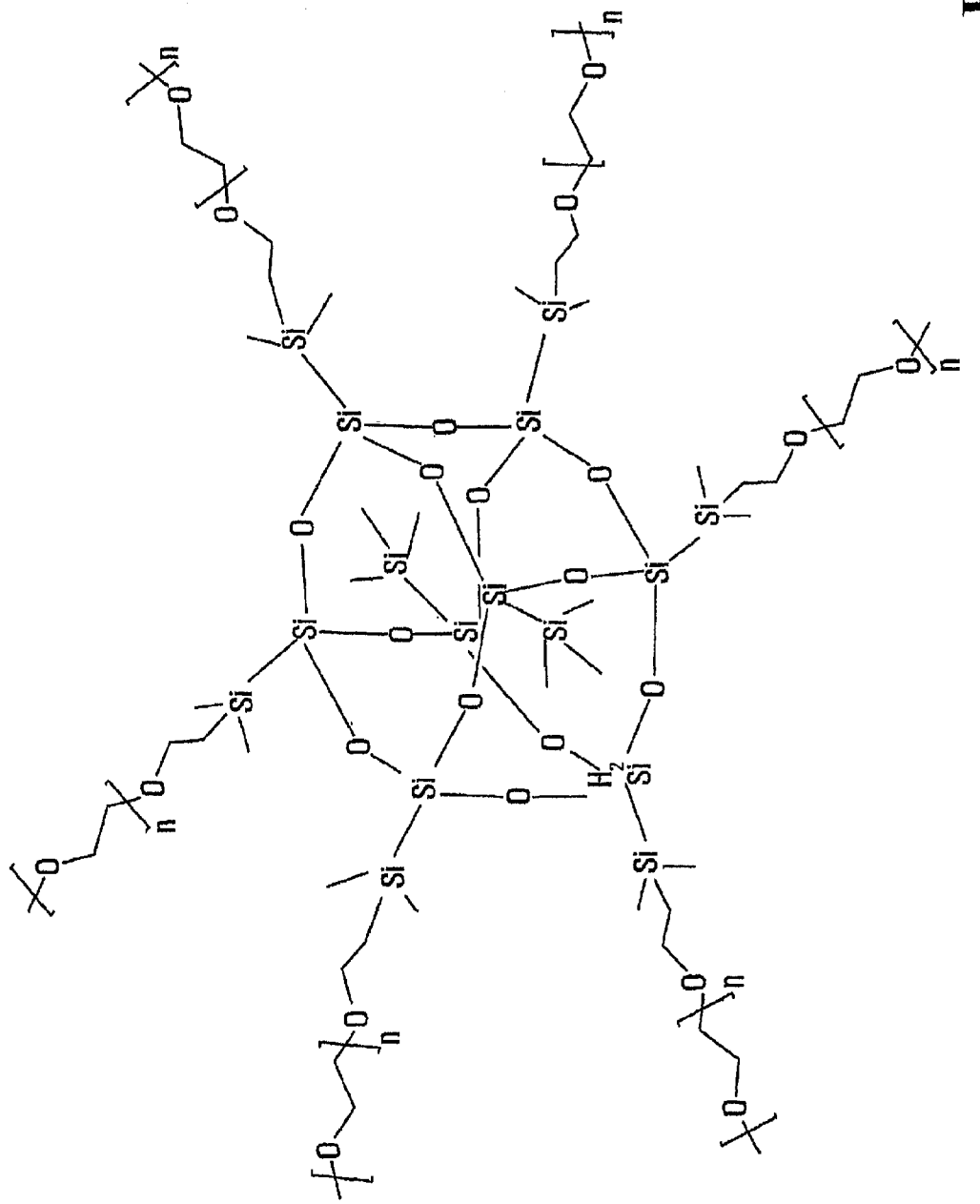
FIGS. 3A and 3B shows chemical structures of exemplary amphiphilic molecules.
Figure 3B:
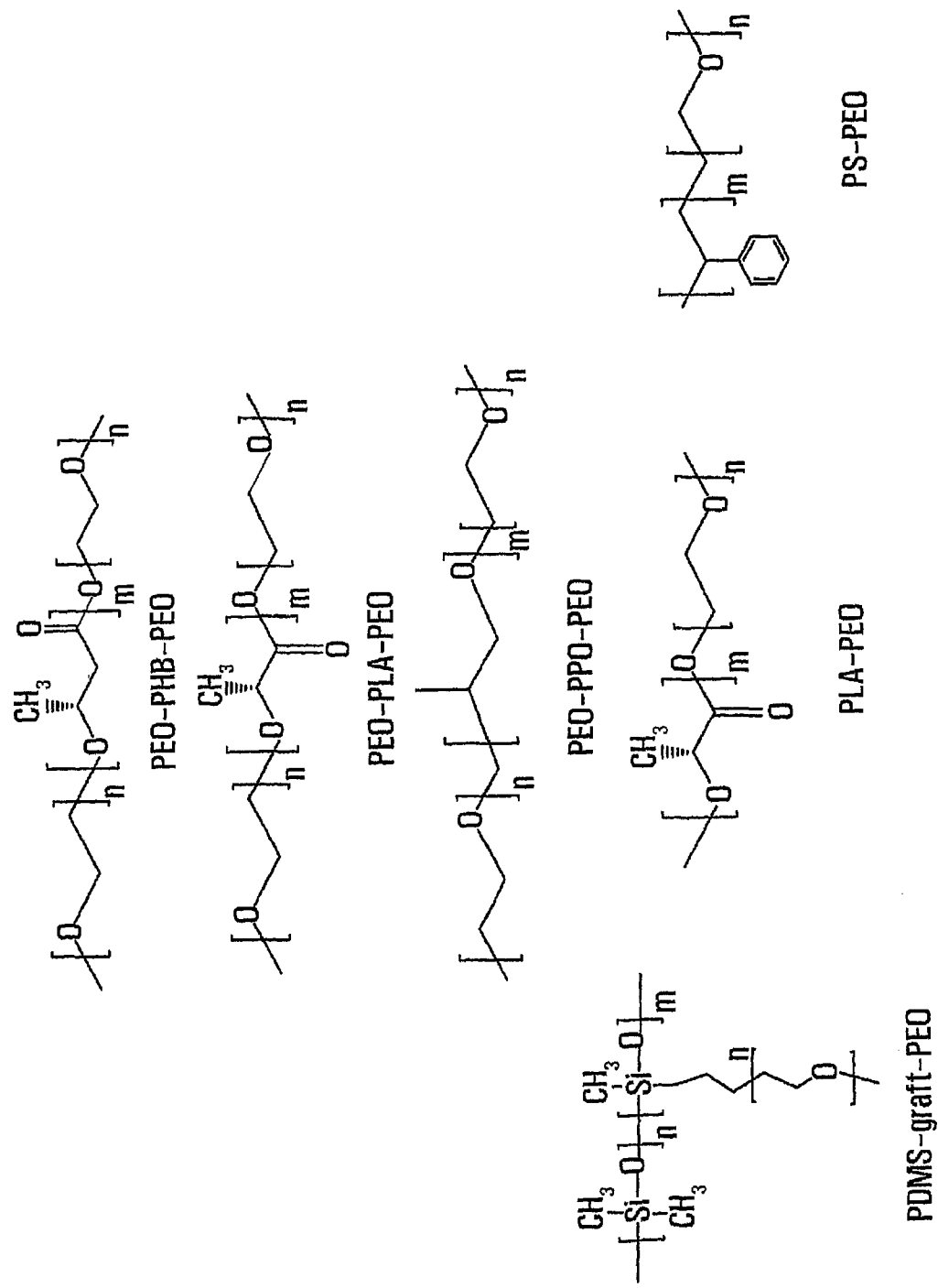

Examples of suitable amphiphilic polymers include polyethylene-oxide (PEO) functionalized polymers, such as polyhedral oligosilsesquioxanes-PEO (POSS-PEO), PEO-polyhydroxybutyrate-PEO (PEO-PHB-PEO), polylactic-acid-PEO (PLA-PEO), PEO-PLA-PEO, PEO-polypropyleneoxide-PEO (PEO-PPO-PEO), polydimethylsiloxane-graft-PEO (PDMS-graft-PEO), polystyrene-PEO (PS-PEO), the chemical structures of which are shown in FIGS. 3A and 3B, wherein each of "m" and "n" may have a value from 3 to 5000.

As can be appreciated, each of the fluorescent polymers and amphiphilic molecules listed above may be capable of being entangled when it is dispersed in a suitable liquid. As can also be appreciated, polymers, unlike crystals, are typically flexible so can be relatively easily entangled. Thus, these polymers may be advantageously used in the particles.

Conveniently, the fluorescent particles like particle 10 are soluble in an aqueous solution and can be used in a wide range of environments and applications, such as bioimaging and biodetection. For example, the fluorescent particles may be used as, or incorporated into, fluorescent probes including labels and tags, as further described below. The particles may be used for imaging, tracking or detecting one or more targets. A target may be a molecule, a cell, or an organism. For example, the particles may be incorporated in, attached to or conjugated to a molecule that is a ligand or a capture molecule that specifically recognizes, binds to, interacts with or is taken up by a target molecule, cell or organism. Alternatively, the particles themselves may act as the probe, provided the particles can bind or adhere to, interact with, or be taken up by the target molecule, cell or organism in such a manner as to allow for visualization of the particles and thus the target molecule, cell or organism.

The entanglement of the molecules also provides a stable outer shell that protects the inner fluorescent core. As a result, the fluorescence properties and performance of the fluorophores, i.e., the fluorescent polymers in the cores of the particles, are not significantly affected by the surrounding environment, so that the particles may be used in a wide range of environments and applications.

The size and the fluorescent property of the structure may vary and can be conveniently controlled or adjusted during the formation process, as will be further described below. In different embodiments, the size of the particles may vary from about 10 nanometers to about 10 micrometers, such as from a few tens of nanometers to a few micrometers. The thickness of the shell region may be in the range of about 5% to about 95% of the particle radius. As can be understood, the particles may be nanoparticles, having sizes in the nanometer range.

Conveniently, as the particles are soluble and stable in water, a clear aqueous solution containing the particles may be obtained. Such a solution may be useful in various applications as can be understood by persons skilled in the art.

Also as can be appreciated, fluorescent polymers may have very short lifetimes, as compared to quantum dots or organic dyes. Thus, particles containing fluorescent polymers may be advantageously used in a fluorescence blinking procedure, such as to track single molecule in live cells. In some embodiments, the fluorescent polymer in the particles may be sensitive to photo irradiation, and thus may be used in a photobleaching application.

Multi-color emission may also be obtained using such particles. As can be understood and discussed above, fluorescent polymers of different emission/absorption spectra may be encapsulated in a single particle. In one embodiment, the different types of fluorescent polymers may have different absorption spectra. Thus, different colors of emission from the particle may be obtained by using different external excitation light sources. In another embodiment, the emission light from one polymer molecule may be absorbed by another polymer molecule in the same particle and cause a further fluorescence emission at a different wavelength from the other polymer molecule. Since energy may be transferred between the different polymers in the same particle, the fluorescent spectra of the particles may be tunable over a wide range, even when they are to be excited by the same light source. For instance, when the same particle contains both blue and green fluorophores and the absorption spectrum of the green fluorophore has a substantial overlap with the emission spectrum of the blue fluorophore, the emission from the blue fluorophore can be absorbed by the green fluorophore, to varying degrees from partial absorption to complete absorption, depending on the extent of overlap between the emission and absorption spectra and the relative amount of each type of fluorescent molecules in the particle. The color of overall emission from the particle may depend on the degree of the intra-particle energy transfer, and may vary from pure blue, green, red, to white or another color. Different emission colors thus may be obtained using one external excitation light source, such as a single UV light source.

The amphiphilic molecules in the particles may be attached to a specific ligand, which can bind to a specific molecule in certain cells or tissues. For instance, a hydrophilic segment of the amphiphilic molecule may be conjugated with the ligand.

The ligand is any detection molecule that can interact with a desired target molecule, cell or organism so as to result in association of the ligand (and therefore the attached particles) and the target. The ligand may specifically bind to a molecule, including a molecule expressed on a cell surface such as a particular cell surface marker or particular cell receptor, including when internalized in a multicellular organism, for example by injection or ingestion. Such binding can in certain circumstances result in uptake of the ligand and attached particle into a cell.

The ligand may be, for example, a nucleotide, a nucleic acid molecule including single-stranded or double-stranded DNA or RNA, a peptide or a protein including a hormone, a peptide ligand, an antibody, a receptor, an antigen, an epitope or a nucleic acid binding protein, a small molecule including an enzyme substrate or an analogue thereof, avidin, streptavidin, biotin, a saccharide including a monosaccharide or a polysaccharide.

The target may be, as stated above, a molecule, a cell or an organism. Where the target is a molecule, the molecule is a molecule that binds to or specifically recognizes the ligand. The molecule may be a nucleic acid, a protein such as a receptor including a cell surface receptor, an enzyme, an antibody, an antigen, a nucleic acid binding protein.

The attachment of a ligand to the particles may be non-covalent, for example electrostatic, or it may be a covalent attachment. The covalent attachment may be direct, meaning there is a covalent bond formed between the amphiphilic molecule of the particle and the ligand, or it may be indirect, for example by a bifunctional spacer or linker group or molecule that covalently bonds with both the amphiphilic molecule of the particle and the ligand.

The ligand may be covalently attached to the particles using known methods. For example, one of the particle or the ligand may be prepared having a reactive functional group that reacts with a complementary functional group in the other of the particle or ligand under conditions that result in formation of a covalent bond between the two complementary functional groups. For example, biotin-avidin, antibody-antigen, and the like. If a bi-functional cross-linker or spacer is used, the linker or spacer may be chosen or prepared to have one reactive functional group that reacts with a complementary functional group on the ligand, and a second reactive functional group that reacts with a complementary functional group on the particle. The linker or spacer may be first reacted with one of the ligand and particle under conditions to form a covalent bond between the linker or spacer and the ligand or particle. The product of the reaction may then be purified, or it may directly be added to the other of the ligand and particle and reacted under conditions that allow for attachment of the ligand to the particle via the spacer or linker.

It will be appreciated that bi-functional spacers or linkers will be chosen depending on the functional groups present in the ligand and the particle, including amino groups, thiol groups, carboxyl groups, carbonyl groups, aldehyde groups. The reactive functional groups in the spacer or linker may be photoreactive or may be an NHS-ester, a maleimide group, a phenyl azide group, a hydrazide group or an isocyanate group. As well, the chosen spacer or linker should not react with the particle in such a manner that, as a result of the reaction, the fluorophore in the particle is no longer functional for the intended purposes.

Consequently, the particles may be used to visualize the cells, to track the cells, or to detect the specific molecules in the cells or tissues.

Different ligands may be attached to the particles. When different types of particles with different fluorescence response characteristics are conjugated with different types of specific ligands, different types of targets may be tracked or detected simultaneously, such as by exciting the samples with light of different wavelengths, or detecting different emission wavelengths.

The particles may be formed by dissolving precursors for both the fluorescent polymer and the amphiphilic molecule in a non-aqueous solvent, such as an organic solvent, to form a solution and mixing the solution with an aqueous liquid such as water. The non-aqueous solvent may be then removed from the mixture. The particles are formed, such as by self-aggregation of the molecules, in the mixture.

Without being limited to any particular theory, it may be expected that when surrounded by water molecules, the hydrophilic segments may tend to move towards the surrounding water molecules and may even form hydrogen bonds with the water molecules. In the process, the hydrophilic segments of the amphiphilic molecule would tangle with one another. In contrast, the hydrophobic segments tend to move away from the water molecules but towards each other. In the process, the hydrophobic segments of both the fluorescent polymer and the amphiphilic molecule would tangle with one another. As a result, the hydrophobic segments are concentrated in the core region of the particle, the hydrophilic segments are concentrated in the shell region of the particle, and the fluorescent polymer is encapsulated by the amphiphilic molecule.

In an exemplary embodiment, precursors for the fluorescent polymer and the amphiphilic molecules may be first prepared, in any suitable manner. Many conventional techniques for preparing various fluorescent polymers and amphiphilic molecules such as amphiphilic polymers are well known to persons skilled in the art, and can be readily implemented in this process. It is noted that a precursor for a polymer or a molecule may include one or more different molecules that will inter react to form the desired molecule, or it may be the same molecule that is to be prepared.

The precursor molecules may be dissolved in a solvent, thus forming a precursor solution containing the fluorescent polymer and amphiphilic molecules for forming the particles to be prepared. The weight ratio of the fluorescent polymer to amphiphilic molecule may be in the range from about 1:100000 to about 95:5. In other words, the weight of the fluorescent polymer may be from about 0.001% to about 95% of the total weight of the fluorescent polymer and the amphiphilic molecule. As will be understood, the weight ratio of the fluorescent polymer to the amphiphilic molecule in the resulting particles may be similar to the ratio in the solution. As can be appreciated, when the precursors or the fluorescent polymer include molecules that is hydrophobic and insoluble in water, a suitable non-aqueous solvent such as an organic solvent may be advantageously used. Any suitable organic solvent in which the selected molecules are soluble may be used. Exemplary organic solvent include tetrahydrofuran (THF), chloroform, dichloromethane, and the like. Other types of solvents in which the selected molecules are soluble may also be used. Suitable solvents in each particular application may vary depending on the particular molecules and precursors involved in the particular application. The solvent may have a relatively high vapor pressure at room temperature, such as when compared to water, the benefit of which will become clear below. To facilitate dissolution and uniform distribution of the molecules, the solution may be agitated such as by sonication or stirring.

The precursor solution may be mixed with an aqueous liquid, such as purified water, to form a liquid mixture.

The aqueous liquid may also be an aqueous solution containing a solute such as a salt, a base, or an acid. The salt may have different ionic strength. The base or acid may be added to adjust the pH of the aqueous solution. The aqueous liquid may also contain an organic solvent such as alcohol. As will be understood by persons skilled in the art, the composition of the aqueous liquid may affect the properties of the particles formed. For instance, the aqueous liquid may be selected to improve control of the particle size or particle size distribution, or both. Depending on the application, additional additives may be added to the solution.

In a different embodiment, the aqueous liquid may be added before all of the other ingredients have been added. Further, the precursor for the amphiphilic molecules may be dissolved in the aqueous liquid, which is then mixed with the precursor polymer solution. In another embodiment, the precursors for the amphiphilic molecule and the fluorescent polymer may be first dissolved in different solvents to form two separate solutions, which are then mixed with an aqueous liquid. It should be noted that changing the sequence of the steps described above or the manner in which the precursor solution is prepared may affect the eventual particle sizes or the size distribution.

In one embodiment, the precursor solution may be added to the aqueous fluid. It may be advantageous to add the precursor solution slowly, such as drop-wise. For instance, adding the precursor solution slowly may improve the homogeneity of the particles. Homogeneity of the particles may refer to the uniform distribution of the particle size or the chemical and physical structures of the particles.

Conveniently, molecular self-aggregation processes may take place automatically in the aqueous liquid mixture, and the entangled structure as illustrated in FIG. 1 may form by self-aggregation at room temperature. As discussed above, the self-aggregation may be at least in part driven by the hydrophobic and hydrophilic properties of the molecules.

In a particular example, the fluorescent polymer may include MEH-PPV and the amphiphilic molecule may include POSS-PEO. In this case, MEH-PPV molecules may concentrate in the core region of the particle and the PEP groups of the POSS-PEO molecules may concentrate in the shell region of the particle. The POSS groups of the POSS-PEO molecules may be entangled with one another and with the MEH-PPV molecules. The PEO groups may be entangled with one another, thus forming a stable shell that encapsulates the MEH-PPV molecules.

The aqueous liquid mixture may be stirred or otherwise agitated to facilitate sufficient mixing and uniform distribution of the molecules, and the entanglement of the molecules.

The average size and size distribution of the particles may be controlled during the formation process. Factors that may affect the sizes of the particles include the types of precursor molecules used such as their chemical structures or molecular weights, the concentrations or ratio of various ingredients in the solutions used, the nature of the solvent, the operating temperature, whether the solution is agitated such as by stirring and extent of agitation such as stirring speed, and the like. The preparation procedure including the sequence and the order of various steps performed may also affect the sizes of the formed particles. Persons skilled in the art will understand that other factors may also affect the sizes of the particles in any given application. The effect of a particular factor on the particle size may be determined by testing using simple testing procedures known to persons skilled in the art. For example, different batches of testing samples may be prepared under different conditions or using different materials or procedures. The particle sizes and size distribution for each batch may be determined using a suitable technique, such as by imaging the test samples and measuring the sizes of the particle images, as illustrated herein.

As can be understood, the fluorescence spectra of the particles may vary depending on the particle size or the density of the particles. While the fluorescent spectra of the particles may be mainly determined by the properties of the fluorescent polymer in the particle, they may also be affected by intermolecular interaction. Thus, the spectra may be fine tuned by adding suitable other molecules in the particle, such as in the core region of the particle, or by selecting different amphiphilic molecules such as those that have different hydrophobic components.

The original, non-aqueous solvent, such as the organic solvent, may be removed from the mixture after the mixture is sufficiently mixed. The solvent may be removed in any suitable manner. A simple technique is to remove the solvent by evaporation. The evaporation technique may be used when the solvent has a relatively high vapor pressure at the evaporation temperature, as compared to water. The high vapor pressure may be advantageous for at least two reasons. One is to limit evaporation of water from the mixture and the other is to evaporate the solvent at a sufficiently high rate, thus reducing the time required to remove the solvent. For example, with many organic solvents such as THF, the evaporation may be carried out at a sufficient rate at room temperature. When desired and appropriate, in some embodiments, the mixture may be heated to accelerate the evaporation process. It should be noted that the evaporation temperature should be low enough to limit evaporation of water.

To speed up the evaporation process, the mixture may be continuously agitated or stirred during evaporation. Further, evaporation may also be accelerated by pumping evaporated solvent vapor away from the surface of the liquid mixture. In some embodiments, stirring may also improve the homogeneity of the particles formed. For example, in some embodiments, stirring may prevent the formation of large aggregates of particles or coagulation of particles. It has been found that the evaporation rate of the organic solvent may also affect the homogeneity of the particles. In some embodiments, a slower evaporation rate may improve the homogeneity of the particles. In one embodiment, the non-aqueous solvent may be completely evaporated over the period of one to two days.

The remaining liquid after evaporation may be subjected to further processing, such as filtration, dilution, drying, or the like, as can be understood by one skilled in the art.

Conveniently, the above procedure may be performed at room temperature or at a different temperature, as the entanglement may occur under such conditions and it is not necessary to heat the solutions or mixed liquid as will be further explained below.

The resulting solution containing the water-soluble fluorescent particles may be used for fluorescence sensing, detecting, labeling or tagging, and other similar purposes. When an organic solvent is used, the solvent may be substantially completely removed from the mixture before use to avoid any undesirable effects caused by the organic solvent.

The fluorescent properties of the resulting particles may be controlled during the formation process, such as by adjusting the ratio of the precursor molecules in the precursor solution. A change in the ratio of the precursors in the precursor solution can result in a change in the ratio of fluorescent molecules to amphiphilic molecules in the resulting particles. For example, as discussed earlier, the weight percentage of the fluorescent molecules may vary from about 0.001 wt % to about 95 wt %. As can be understood, the fluorescence intensities of the resulting particles may depend on this ratio. Thus, the fluorescence intensities of the particles may be adjusted by adjusting this ratio.

The fluorescent particles formed may be extracted from the final solution, such as by drying, and stored for future use. However, as can be appreciated, the fluorophores are typically used in a liquid environment, often an aqueous environment, in biological or biochemical applications. Thus, before use, the dried particles may be dissolved in an aqueous solution again. While the dried particles may coagulate, once re-dissolved, the coagulated particles will disintegrate and again form relatively uniformly sized particles. As can be appreciated, in some applications, it is desirable that the fluorescent particles are of uniform sizes.

A solution containing particles that have different emission spectra can be obtained by dissolving different types of particles in the same aqueous fluid such as purified water, where each type of particles are prepared in accordance with an embodiment of the present invention but has a distinct emission spectrum. For example, each type of particles may exhibit single-color emission but different types of particles emit light of different colors. Thus, the solution may have multi-color fluorescence emission properties, and may be used for multi-target probing.

As now can be appreciated, to form the water-soluble fluorescent particles according to the exemplary process described above, it is not necessary to form any stable chemical bonds between the fluorescent polymer and the amphiphilic molecules. It is also not necessary to cross-link the amphiphilic molecules. As can be understood, the entanglement of molecules involve random configuration, twisting and entwining of the entangled molecules, with random intermolecular interaction points. The atoms or segments of one entangled molecule are randomly located with respect to those of another entangled molecule and there are no strong chemical bonds, i.e., ionic and covalent bonds, between the two entangled molecules, although weaker bonds may form between segments of the different molecules. It is believed that the entanglement of the molecules provides sufficient stability of the particle structures, even though there are no strong chemical bonds among the entangled molecules. As a result, complicated processing steps or steps that involve chemical reactions at high temperatures may be avoided in the process. Thus, the process may be carried out at the room temperature and ambient pressure, and in a small number of simple steps.

Whether entanglement among the molecules exists may be determined based on various suitable techniques, including conventional techniques known to one skilled in the art, depending on the application. It may be possible to image the molecular structures in the particles, or to determine whether ionic or covalent bonds have formed between the molecules, so that the existence of entanglement may be accessed either directly or indirectly. For example, it is also possible to assess the existence or degree of molecular entanglement based on molecular dynamics simulation, see e.g., Z. Q. Zhang and X. Z. Yang, "The effect of chain interpenetration on an ordering process in the early stage of polymer crystal nucleation", *Polymer,* 2006, vol. 47, no. 14, pp. 5213-5219; based on differential scanning calorimetry (DSC), see e.g. J. J. Hao et al., "Synthesis and comparison of hyperbranched aromatic polyimides having the same repeating unit by AB(2) self-polymerization and A(2)+B−3 polymerization", *Macromolecules,* 2003, vol. 36, no. 10, pp. 3519-3528; based on rheological property measurement, see e.g. R. N. Shroff and H. Mavridis, "Assessment of NMR and rheology for the characterization of LCB in essentially linear polyethylenes", *Macromolecules,* 2001, vol. 34, no. 21, pp. 7362-7367; or based on NMR measurement, see e.g. A. Charlesby, "Analysis Of Macromolecular Structures By Pulsed NMR", *Radiation Physics And Chemistry,* 1992, vol. 39, no. 1, pp. 45-51. The contents of each of the above cited references are incorporated herein by reference.

As can be appreciated, the exemplary processes described herein are easy to perform and do not require extensive heating, expensive equipment, or strict or difficult handling procedures.

As the size of the particles and the thickness of the shells of the particles can be adjusted and controlled during the preparation process, the particles may have particle sizes and shell thicknesses selected to reduce energy transfer from one particle to another. For example, inter-particle energy transfer may depend on the fluorescent spectra of the interacting particles and the distance between them. Thus, by adjusting the concentration of the particles in the solution and the shell thickness, the inter-particle energy transfer may be controlled.

EXAMPLES

Example 1

A Sample I solution was prepared as follows.

A solution of MEH-PPV in a THF solvent was prepared. The concentration of MEH-PPV in the solution was 1 mg/g.

20 mg of POSS-PEO was added to 20 mg of the MEH-PPV solution. The solution was diluted to 1 ml by adding THF to form the precursor solution.

The precursor solution was mixed with 10 g of deionized water in a 20 ml glass bottle. The precursor solution was added drop-wise to the water in the bottle over a two-minute period, during which time the contents of the bottle were sonicated. After mixing, the contents of the bottle were further sonicated for five more minutes.

The mixed liquid was stirred at room temperature for two days to remove THF by evaporation, using a magnetic stirrer.

The resulting solution was filtered with a 1-µm filter to remove aggregated particles. The filtered solution was the Sample I solution, which contained fluorescent nanoparticles. In the nanoparticles, the MEH-PPV molecules were encapsulated by the POSS-PEO molecules.

The ratio of MEH-PPV to POSS-PEO in the precursor solution was about 0.1 wt %. The concentration of POSS-PEO in the mixed liquid was about 0.2 wt %.

Figure 4A:
FIGS. 4A and 4B are confocal microscopic images of exemplary fluorescent particles in an aqueous solution.
Figure 4B:
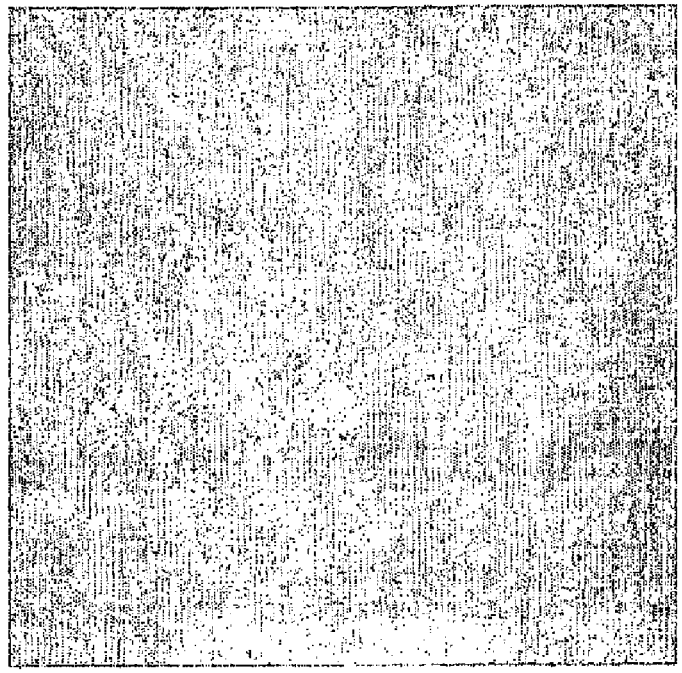

FIGS. 4A and 4B respectively show confocal images of particles in Sample I solution, measured with a LEICA DM IRE2™ Inverted Research Microscope. FIG. 4A shows a fluorescent image and FIG. 4B shows a transmitted light image. The bright dots are images of the particles. As can be seen, the sizes, shapes, and brightness of these dots are relatively uniform, indicating that the sizes, shapes and luminance of the imaged particles were quite uniform. These images indicate that the average particle size in Sample I solution was about 200 nm.

Example 2

A Sample II solution was prepared similarly as the Sample I solution, except that the amount of the MEH-PPV THF solution used to form the precursor solution was 10 mg. As a result, the ratio of MEH-PPV to POSS-PEO in the precursor solution was about 0.05 wt %.

Figure 5A:
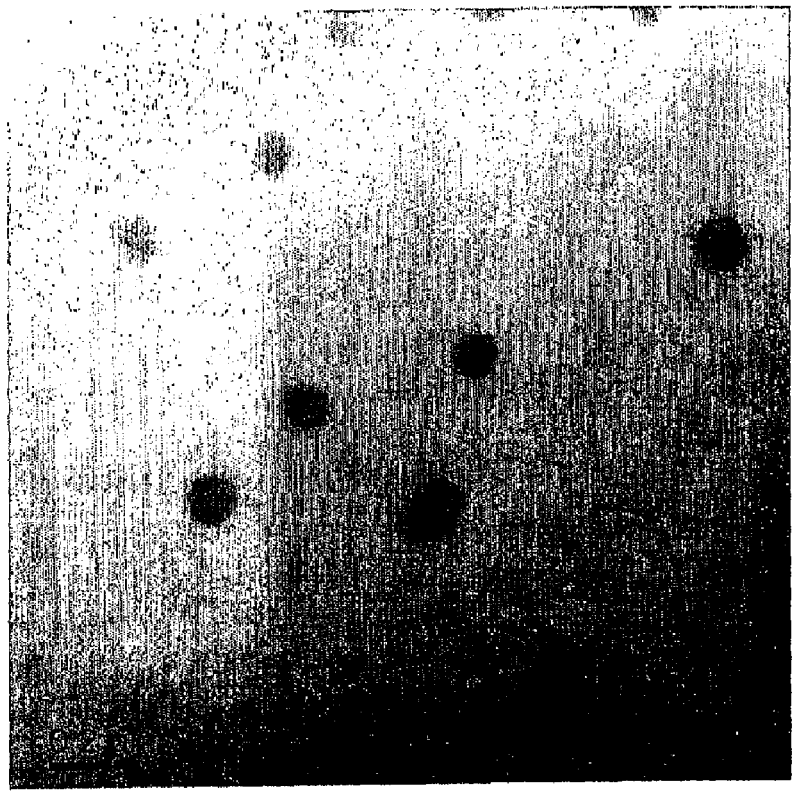

FIG. 5A shows a TEM image taken from the Sample II solution. The dark dots are images of the particles. Judging from the image, the particle sizes vary from about 140 nm to about 165 nm.

Example 3

A Sample III solution was prepared similarly as the Sample I solution, except that the amount of the MEH-PPV THF solution used was 30 mg. As a result, the ratio of MEH-PPV to POSS-PEO in the precursor solution was about 0.15 wt %.

Figure 5B:
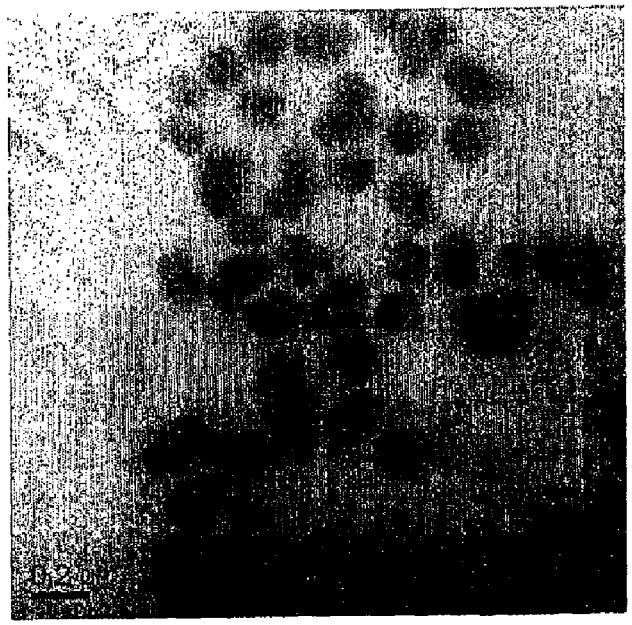

FIG. 5B shows a TEM image taken from the Sample III solution. The dark dots are images of the particles. The images of FIGS. 5A and 5B indicate that the particle sizes in Sample II solution and Sample III solution were similar.

Examples 4 to 6

Sample IV, V, and VI solutions were respectively prepared similarly as Sample I, II and III solutions, except that MEH-PPV polymer was replaced with C6PF polymer and the nanoparticles in the Sample solutions had C6PF as the fluorophore, instead of MEH-PPV.

Examples 7 to 9

Sample VII, VIII, IX solutions were prepared similarly as Sample I, II, and III solutions respectively, except that MEH-PPV polymer was replaced with BP-PPV polymer and the nanoparticles in the sample solutions had BP-PPV as the fluorophore, instead of MEH-PPV.

Examples 10 to 18

Sample X to XVIII solutions were respectively prepared similarly as Sample I to IX solutions, except that the POSS-PEO polymer was replaced with PEO-PHB-PEO polymer and the nanoparticles in the sample solutions had PEO-PHB-PEO as the encapsulating molecules, instead of POSS-PEO.

Example 19

A Sample XIX solution was prepared as follows.

A C6PF solution was prepared by dissolving C6PF in a THF solvent. The concentration of C6PF in the C6PF solution was 1 mg/g.

A BP-PPV solution was prepared by dissolving BP-PPV in a THF solvent. The concentration of BP-PPV in the BP-PPV solution was 1 mg/g.

20 mg of POSS-PEO, 20 mg of the C6PF solution, and 20 mg of the BP-PPV solution were mixed together. The mixed solution was diluted to 1 ml by adding THF to form the precursor solution.

The precursor solution was added to 10 g of deionized water in a 20 ml glass bottle. The precursor solution was added drop-wise to the bottle over a two-minute period, during which time the contents of the bottle were sonicated. After mixing, the contents of the bottle were further sonicated for five more minutes.

The mixed liquid in the bottle was stirred at room temperature for two days to remove THF by evaporation, using a magnetic stirrer.

The resulting solution was filtered with a 1-μm filter to remove aggregated particles. The filtered solution was the Sample XIX solution, which contained fluorescent nanoparticles. The nanoparticles had both C6PF and BP-PPV polymers in the core region, encapsulated by the POSS-PEO polymer.

The ratio of each of C6PF and BP-PPV to POSS-PEO in the precursor solution was about 0.1 wt %.

Example 20

The Sample VII solution was added with small amount of 1M HCl or 1M NaOH to adjust its pH value from neutral to about 3 to about 10.

Figure 6:
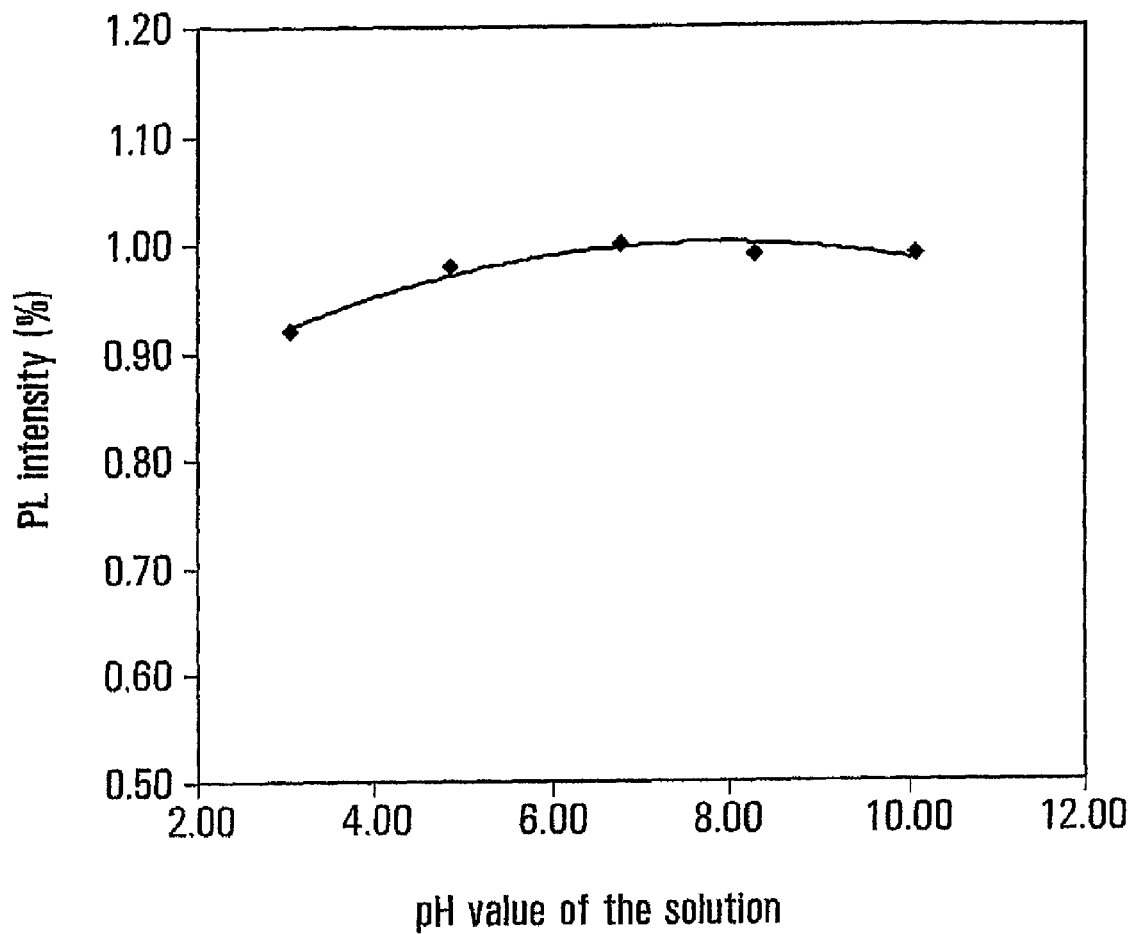
FIG. 6 is a line graph showing the photoluminescent (PL) emission intensity of exemplary fluorescent particles in an aqueous solution, as a function of the pH values of the solution.

The PL emission intensities of fluorescent particles in the solutions of different pH were measured, and shown in FIG. 6. The squares are measured points and the line is a fit of the points. As can be seen, the emission intensity was substantially constant over a wide pH range. Even when the pH was as low as about 3, the PL intensity only decreased by about 8% from the value in a neutral solution. It is expected that the high fluorescence stability is due to the fact that the fluorescent polymers are in a hydrophobic environment isolated from the surrounding water phase. Thus, changes in the solution conditions, such as its pH value, which may affect the PEO groups, would have relatively small influence on the fluorescent polymers in the core of the particles. The test results thus show that the fluorescent polymer was indeed encapsulated.

Example 21

A test solution containing fluorescent nanoparticles was prepared, in a similar procedure as described in Example I, but the mixed liquid used to form the particles contained 50 mg of POSS-PEO, 0.1 mg of MEH-PPV and 10 ml of deionised water.

A cell culture medium was prepared. 1 ml of the cell culture medium was mixed with 200 μl of the test solution. Microglial cells were dispersed in the resulting mixture, which was then imaged at 2, 6, 12 and 24 hours thereafter respectively, using a confocal microscope. After 24 hours, the cultured microglial cells were fixed for two hours with formalin according a standard procedure. At the 26-hour interval, the mixture was imaged again.

Figures 7A, 7B, 7C:
FIGS. 7A to 7O are confocal microscopic images of microglial cells cultured in aqueous solutions containing exemplary fluorescent particles.
Figures 7D, 7E, 7F:
Figures 7G, 7H, 7I:
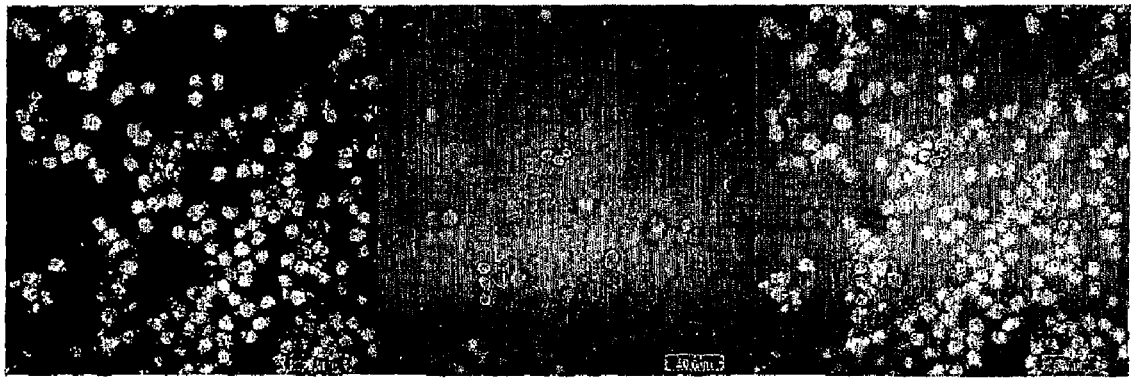
Figures 7J, 7K, 7L:
Figures 7M, 7N, 7O:
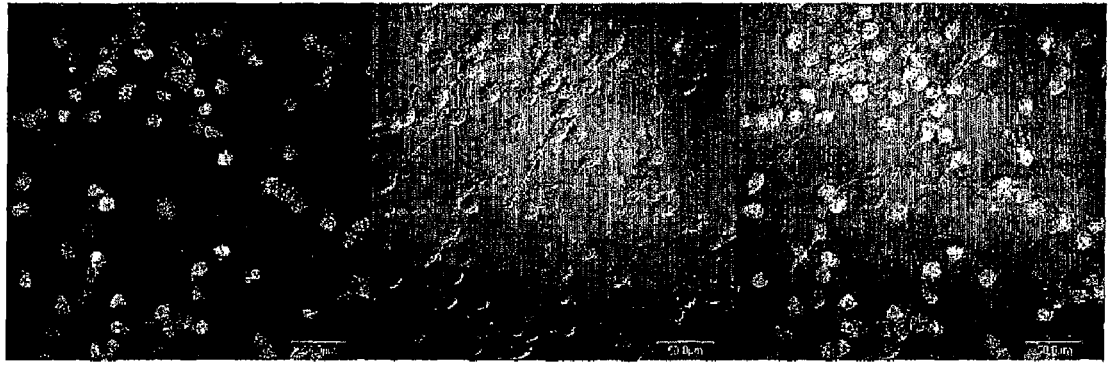

Some sample images obtained at different intervals are shown in FIGS. 7A to 7O. Briefly, FIGS. 7A to 7C show images of the mixture taken at the 2-hour interval; FIGS. 7D to 7F show images of the mixture taken at the 6-hour interval; FIGS. 7G to 7I show images of the mixture taken at the 12-hour interval; FIGS. 7J to 7L show images of the mixture taken at the 24-hour interval; and FIGS. 7M to 7O show images of the mixture taken after the cells had been cultured for 24 hours and then fixed for two hours with formalin. FIGS. 7A, 7D, 7G, 7J and 7M show fluorescent images of the mixture, where the bright dots indicate the locations of the fluorescent particles. FIGS. 7B, 7E, 7H, 7K and 7N show microscopy images of the mixture, where the locations of the cells are indicated. Each of FIGS. 7C, 7F, 7I, 7L and 7O shows the superposition of the two images to its left, that is, the fluorescent and microcopy images taken at the same time for the same area of the mixture.

As can be appreciated from FIG. 7O, almost all microglial cells uptook the fluorescent nanoparticles, as the locations of the cells and the fluorescent particles coincide. It is expected that the fluorescent nanoparticles were up-taken by the cells through a pinocytotic process.

The obtained cell images indicate that the live cell density in the mixture was constant over the observed period of 24 hours, as the number of cells in a same area did not change much in these images. This result indicates that the fluorescent nanoparticles were not cytotoxic to the cells.

The images further indicate that formalin fixation of the cells did not significantly affect the fluorescent properties of the nanoparticles in the cultured cells.

As can be appreciated, the test results illustrate the potential applicability of these nanoparticles in bio-imaging or detection for immunoassay, or in delivery systems as tracers of drug, gene, cells or the like.

In addition, the optical properties of the sample particles were measured using optical absorption spectroscopy and fluorescent spectroscopy. FIGS. 8A to 8E show respective UV and PL spectra measured from the sample solutions and comparison samples.

Figure 8A:
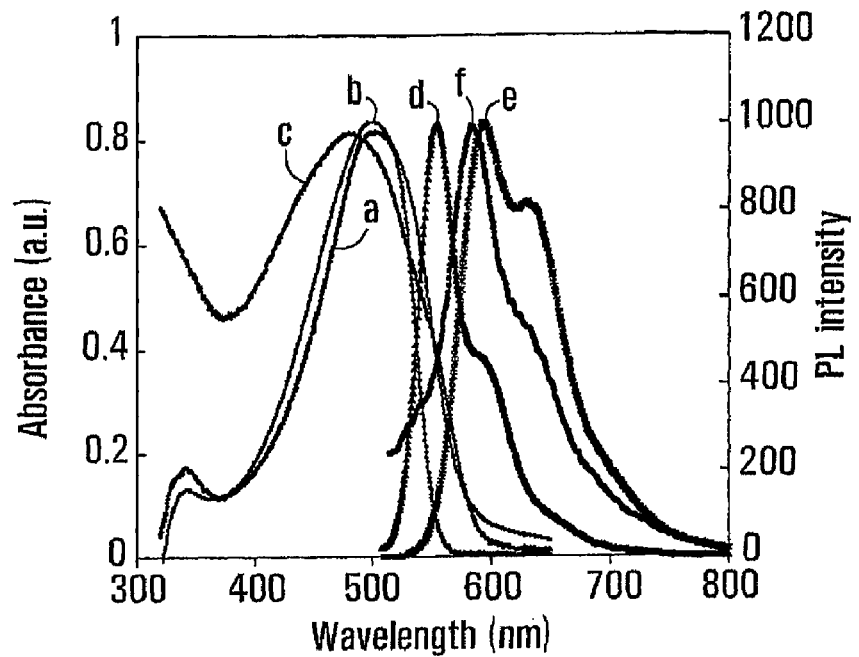
FIGS. 8A to 8D are line graphs showing the ultraviolet (UV) and PL spectra of fluorescent polymers in different environments.

FIG. 8A shows the measured result for MEH-PPV polymers in different environments. The spectra lines are labeled as follows:
(a) UV spectrum of MEH-PPV polymer dissolved in a THF solvent;
(b) UV spectrum of a MEH-PPV film;
(c) UV spectrum of the fluorescent particles in Sample I solution;
(d) PL spectrum of MEH-PPV polymer in a THF solvent;
(e) PL spectrum of a MEH-PPV film (PL); and
(f) PL spectrum of the fluorescent particles in Sample I solution.

The MEH-PPV film was prepared by spinning a MEH-PPV-THF solution onto a quartz plate.

The results indicated that the fluorescent polymer in the particles, the film or the solution had similar configuration. However, as can be appreciated, the maximum absorption wavelength of the fluorescent particles in Sample I solution ("c") is blue shifted, as compared to the absorption spectra of MEH-PPV in THF solvent ("a") and in the sample film ("b"). The PL intensity peak for Sample I solution ("f") is located between the peaks for the THF solution ("d") and the film ("e"), but much closer to the peak for the film. The relative quantum yield of the particles in Sample I solution was about 5% to 10% (based on $10^{-5}$ quinine sulfate in 0.10 M $H_2SO_4$ as standard).

Figure 8B:
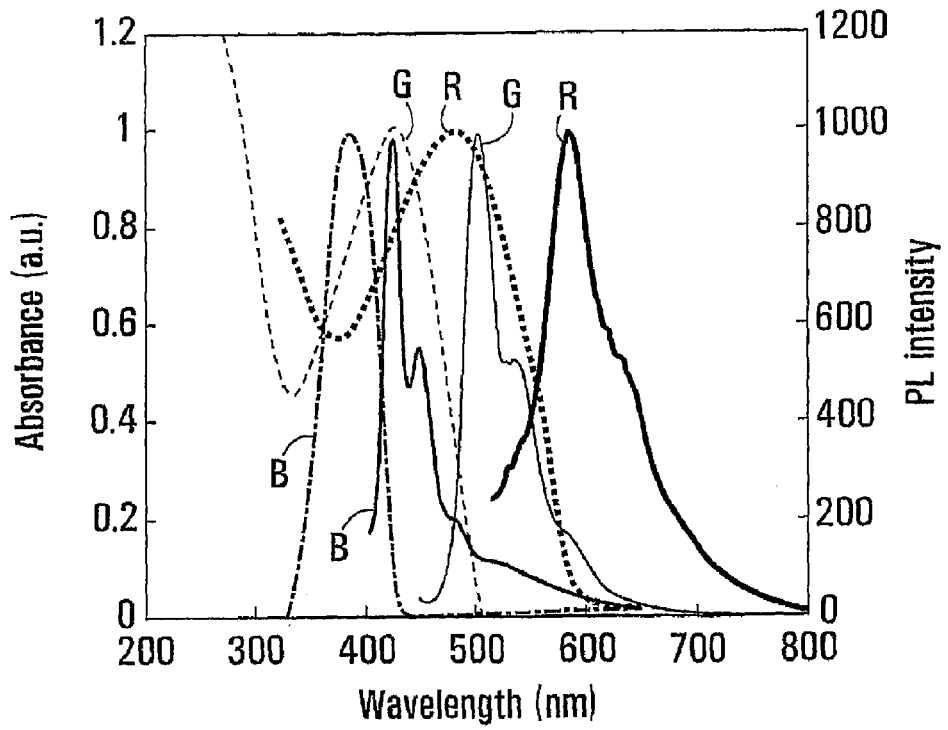

FIG. 8B shows the UV (solid lines) and PL (broken lines) spectra of sample fluorescent particles in Sample I solution (R), Sample IV solution (B), and Sample VII solution (G), which respectively emitted light of the general color of red, blue, or green on excitation. As can be seen, particles having different fluorescent polymers emitted light of different colors under different wavelengths of excitation. The relative quantum yields for Sample IV solution, Sample VII solution, and Si-PPV/POSS(0.1%)-PEO were 30%, 62%, and 90%, respectively.

Figure 8C:
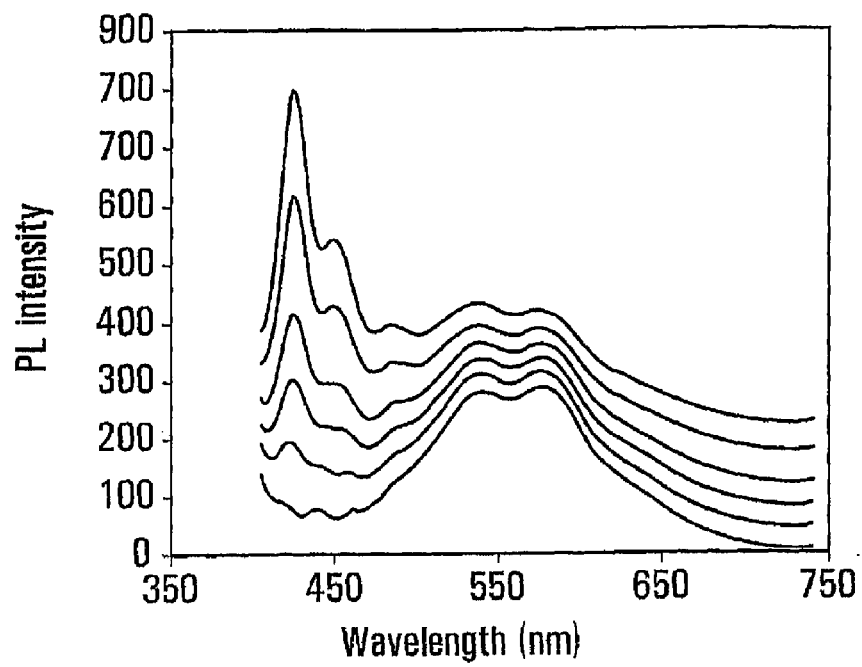

FIG. 8C shows the measured PL spectra of fluorescent particles in mixtures of Sample I solution and Sample IV solutions at different mixing ratios, except the bottom line which was taken from a pure Sample I solution. The ratios of Sample IV solution/Sample I solution in the mixtures were respectively, 20%, 10%, 4%, 2%, and 1%, in the order from the top line to the line next to the bottom line in FIG. 8C. As can be seen, the emission intensity decreases as the percentage of Sample II solution increases.

FIG. 8C illustrates that when two or more types of fluorescent particles are mixed in a solution at a certain mixing ratio, the fluorescence of the mixture solution is a sum of the individual fluorescence of different particles. As can be seen, the intensity of blue emission gradually increases with increasing percentage of Sample IV solution (C6PF/POSS-PEO particles). When the percentage of the C6PF/POSS-PEO sample was increased to 10%, emission from C6PF/POSS-PEO sample became dominant because of its intense fluorescence. It appeared that there was no energy transfer from the C6PF/POSS-PEO particles to the MEH-PPV/POSS-PEO particles. Without being limited to a particular theory, it is expected that lack of energy transfer has two reasons: (1) the particle sizes were in the range of 100 to 200 nm, which is beyond the förster energy transfer range; and (2) the percentage of the C6PF/POSS-PEO particles was too low for significant energy transfer.

The above results suggest that it is possible to adjust the fluorescence spectra of the particles, not only their wavelength ranges and intensities but also their shapes.

Another advantage of the mixed fluorescent particles is that when light of different excitation wavelengths is used to excite the mixed particles, the particles may exhibit very different emission spectra. For example, when a mixture containing C6PF/POSS-PEO and MEH-PPV/POSS-PEO particles is excited at 390 nm, both C6PF/POSS-PEO and MEH-PPV/POSS-PEO particles would emit light. However, when the mixture is excited at 490 nm, only MEH-PPV/POSS-PEO particles will emit light.

Figure 8D:
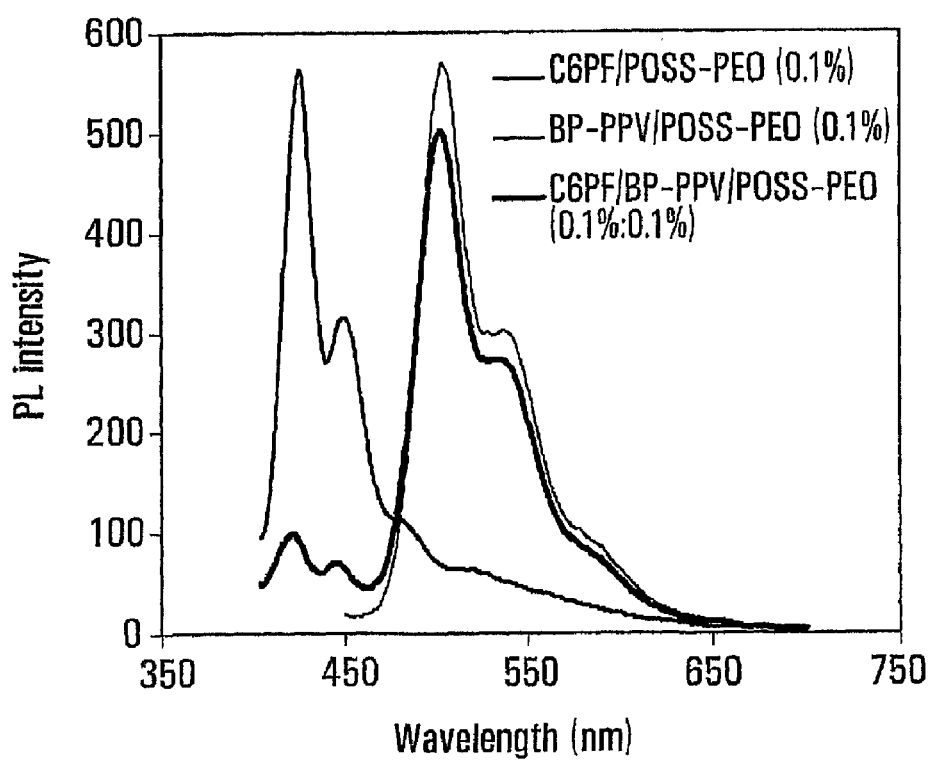

FIG. 8D shows PL spectra for Sample IV solution (line on the left), Sample VII solution (thin line), and a mixture of the two solutions at a ratio of 1:1 (thick line).

This figure illustrates the energy transfer behavior between blue chromophore and green chromophore. In the particles formed from the mixture of the two solutions, each particle had both blue chromophore and green chromophore. When these particles were irradiated with a light of short wavelength, both blue and green chromophores emitted light. However, as can bee seen, most of the energy of the excited blue chromophore was transferred to the green chromophore and the emission from the particles came mainly from the green chromophores. This result demonstrates that it is possible to selectively excite either the green chromophore (using light of long wavelength) or both the blue and green chromophores.

Other features, benefits and advantages of the embodiments described herein not expressly mentioned above can be understood from this description and the drawings by those skilled in the art.

The contents of each reference cited above are hereby incorporated herein by reference.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A water-soluble fluorescent particle, comprising:
a fluorescent polymer comprising a fluorophore and a hydrophobic segment attached to said fluorophore; and
an amphiphilic molecule comprising hydrophilic segments and hydrophobic segments, said hydrophilic segments of said amphiphilic molecule being entangled with one another, said hydrophobic segments of said fluorescent polymer and said amphiphilic molecule being entangled with one another,
wherein the entangled segments form a shell encapsulating said fluorophore and at least some of said hydrophilic segments are exposed to render said particle soluble in water.

2. The water-soluble fluorescent particle of claim 1, wherein said fluorescent polymer comprises at least one of arylene, heteroarylene, arylene vinylene, heteroarylene vinylene, arylene ethylene, or heteroarylene ethylene.

3. The water-soluble fluorescent particle of claim 2, wherein said at least one of arylene, heteroarylene, arylene vinylene, heteroarylene vinylene, arylene ethylene, and heteroarylene ethylene is substituted.

4. The water-soluble fluorescent particle of claim 2, wherein said at least one of arylene, heteroarylene, arylene vinylene, heteroarylene vinylene, arylene ethylene, and heteroarylene ethylene is unsubstituted.

5. The water-soluble fluorescent particle of claim 2, wherein at least one ring carbon atom of said heteroarylene group has been substituted by one of O, S, N, Si, and P atoms.

6. The water-soluble fluorescent particle of claim 2, wherein said arylene group is bonded to another arylene group by a single bond, or connected to another arylene group by a connecting group, said connecting group being O, S, Si, N, P, a substituted alkylene, or a non-substituted alkylene.

7. The water-soluble fluorescent particle of claim 1, wherein said fluorescent polymer comprises at least one of phenylene, thienylene, fluorenylene, spirobifluorenylene, indenofluorenylene, pyridylene, bipyridylene, carbazoylene, indenocarbazolylene, benzothiazolylene, oxadiazolylene, alkyl, alkoxy, alkenyl, alkynyl, alkylthio, alkylamino, dialkylamino, arylamino, diarylamino, aryl ether, heteroaryl ether, aryl thioether, heteroaryl thioether, hydrogen, halogen, cyano, nitro, carbony, thionyl, sulphonyl, perfluoroalkyl, and amino group comprising a heteroaryl group.

8. The water-soluble fluorescent particle of claim 1, wherein said fluorescent polymer comprises one or more of poly(2,5-bisdimethyldecylsilyl)-1,4-phenylene vinylene; poly(2-methoxy-5-2'-ethyl-hexyloxy-1,4-phenylene vinylene); poly(9,9-dihexyl-fluorene-2,7-diyl); and poly(2-(2'-phenyl-4',5'-di(3"-methyl-butyl)-phenyl-1,4-phenylenevinylene)).

9. The water-soluble fluorescent particle of claim 1, wherein said amphiphilic molecule comprises one or more of lipids and polymers.

10. The water-soluble fluorescent particle of claim 1, wherein said amphiphilic molecule is selected from:
  (a) a copolymer having a backbone, wherein said backbone comprises a hydrophobic block;
  (b) a copolymer having a backbone and a graft segment attached to said backbone, wherein
    (i) said backbone comprises a hydrophilic segment and said graft segment comprises a hydrophobic segment, or (ii) said backbone comprises a hydrophobic segment and said graft segment comprises a hydrophilic segment, or (iii) each one of said backbone and said graft segment comprises both a hydrophilic segment and a hydrophobic segment;

(c) a hyperbranched polymer comprising a hydrophilic segment and a hydrophobic segment; and (d) a dendritic polymer comprising a hydrophilic segment and a hydrophobic segment.

11. The water-soluble fluorescent particle of claim 1, wherein said amphiphilic molecule comprises a polyethylene-oxide (PEO) functionalized polymer.

12. The water-soluble fluorescent particle of claim 11, wherein said PEO functionalized polymer comprises one or more of polyhedral oligosilsesquioxanes-PEO (POSS-PEO), PEO-polyhydroxybutyrate-PEO (PEO-PHB-PEO), polylactic-acid-PEO (PLA-PEO), PEO-PLA-PEO, PEO-polypropyleneoxide-PEO (PEO-PPO-PEO), polydimethylsiloxane-graft-PEO (PDMS-graft-PEO), and polystyrene-PEO (PS-PEO).

13. The water-soluble fluorescent particle of claim 1, wherein said amphiphilic molecule encapsulates a plurality of fluorescent polymers, each one of said fluorescent polymers having a distinct fluorescence response.

14. The water-soluble fluorescent particle of claim 13, wherein each one of said fluorescent polymers has a distinct fluorescence emission spectrum.

15. The water-soluble fluorescent particle of claim 13, wherein each one of said fluorescent polymers has a distinct fluorescence absorption spectrum.

16. The water-soluble fluorescent particle of claim 1, having a particle size between about 10 nanometers and about 10 micrometers.

17. The water-soluble fluorescent particle of claim 1, further comprising a ligand for attaching said particle to a target.

18. The water-soluble fluorescent particle of claim 17, wherein said ligand comprises at least one of a nucleotide, single-stranded DNA, double-stranded DNA, single-stranded RNA, double-stranded RNA, a peptide, a protein, a hormone, an antibody, a receptor, an antigen, an epitope, a nucleic acid binding protein, a molecule, an enzyme substrate or an analogue thereof, avidin, streptavidin, biotin, a monosaccharide, and a polysaccharide.

19. The water-soluble fluorescent particle of claim 17, wherein said target comprises at least one of a molecule, a cell, and an organism.

20. A fluorescent probe comprising the water-soluble fluorescent particle of claim 1.

21. The fluorescent probe of claim 20, comprising a plurality of water-soluble fluorescent particles, each having a distinct fluorescence response.

22. The fluorescent probe of claim 21, wherein each one of said water-soluble fluorescent particles has a distinct fluorescence emission spectrum.

23. The fluorescent probe of claim 21, wherein each one of said water-soluble fluorescent particles has a distinct fluorescence absorption spectrum.

24. A solution comprising the water-soluble fluorescent particle of claim 1 dissolved in water.

25. The solution of claim 24, comprising a plurality of water-soluble fluorescent particles, each having a distinct fluorescence response.

26. The solution of claim 25, wherein each one of said water-soluble fluorescent particles has a distinct fluorescence emission spectrum.

27. The solution of claim 24, wherein each one of said water-soluble fluorescent particles has a distinct fluorescence absorption spectrum.

28. The water-soluble fluorescent particle of claim 1, wherein said particle has a particle radius, and the shell formed of said entangled segments has a thickness of about 5% to about 95% of said particle radius.

29. A water-soluble fluorescent particle, comprising:

a fluorescent polymer comprising a fluorophore and a hydrophobic segment attached to said fluorophore, wherein said fluorescent polymer is selected from poly (2,5-bisdimethyldecylsilyl)-1,4-phenylene vinylene; poly(2-methoxy-5-2'-ethyl-hexyloxy-1,4-phenylene vinylene); poly(9,9-dihexyl-fluorene-2,7-diyl); and poly(2-(2'-phenyl-4',5'-di(3"-methyl-butyl)-phenyl-1, 4-phenylenevinylene)); and an amphiphilic molecule comprising hydrophilic segments and hydrophobic segments, said hydrophilic segments of said amphiphilic molecule being entangled with one another, said hydrophobic segments of said fluorescent polymer and said amphiphilic molecule being entangled with one another, wherein said amphiphilic molecule comprises a polyethylene-oxide (PEO) functionalized polymer selected from polyhedral oligosilsesquioxanes-PEO (POSS-PEO), PEO-polyhydroxybutyrate-PEO (PEO-PHB-PEO), polylactic-acid-PEO (PLA-PEO), PEO-PLA-PEO, PEO-polypropyleneoxide-PEO (PEO-PPO-PEO), polydimethylsiloxane-graft-PEO (PDMS-graft-PEO), and polystyrene-PEO (PS-PEO), wherein said amphiphilic molecule encapsulates said fluorescent polymer and at least some of said hydrophilic segments are exposed to render said particle soluble in water.

* * * * *